(12) United States Patent
Steinke

(10) Patent No.: US 10,293,171 B2
(45) Date of Patent: May 21, 2019

(54) METHOD AND APPARATUS FOR INTERLOCKING STIMULATION PARAMETERS FOR NEUROMODULATION

(71) Applicant: Boston Scientific Neuromodulation Corporation, Valencia, CA (US)

(72) Inventor: G. Karl Steinke, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 39 days.

(21) Appl. No.: 15/432,514

(22) Filed: Feb. 14, 2017

(65) Prior Publication Data

US 2017/0266455 A1 Sep. 21, 2017

Related U.S. Application Data

(60) Provisional application No. 62/310,306, filed on Mar. 18, 2016.

(51) Int. Cl.
*A61N 1/372* (2006.01)
*A61N 1/05* (2006.01)
(Continued)

(52) U.S. Cl.
CPC ....... *A61N 1/37247* (2013.01); *A61N 1/0534* (2013.01); *A61N 1/0551* (2013.01);
(Continued)

(58) Field of Classification Search
CPC .............. A61N 1/37247; A61N 1/0534; A61N 1/0551; A61N 1/36128; A61N 1/36171;
(Continued)

(56) References Cited

U.S. PATENT DOCUMENTS 6,516,227 B1 2/2003 Meadows et al.
7,783,353 B2 8/2010 Libbus et al.
(Continued)

FOREIGN PATENT DOCUMENTS

| EP | 2567729 A1 | 3/2013 |
|---|---|---|
| WO | WO-2016172239 A1 | 10/2016 |
| WO | WO-2017160442 A1 | 9/2017 |

OTHER PUBLICATIONS

Carcieri, Stephen, et al., "Method and Apparatus for Programming Deep Brain Stimulation Devices", U.S. Appl. No. 62/150,935, filed Apr. 22, 2015.
(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

An example of a system for delivering neurostimulation may include a display and an interface control circuit. The interface control circuit may be configured to define a stimulation waveform according to which the neurostimulation is delivered. The stimulation waveform is defined by waveform parameters including one or more user-adjustable parameters. The interface control circuit may include a parameter selector, an effect analyzer, and a parameter generator. The parameter selector may be configured to present values for each user-adjustable parameter on the display and allow the user to select a value for each user-adjustable parameter from the presented values. The effect analyzer may be configured to estimate an interactive effect of different stimuli of the neurostimulation. The parameter generator may be configured to select a rate rule based on the estimated interactive effect and to generate the values for each user-adjustable parameter according to the selected rate rule.

20 Claims, 9 Drawing Sheets

(51) Int. Cl.
*A61N 1/36* (2006.01)
*G06F 19/00* (2018.01)
*G16H 40/63* (2018.01)

(52) U.S. Cl.
CPC ..... *A61N 1/36128* (2013.01); *A61N 1/36171* (2013.01); *A61N 1/36185* (2013.01); *G06F 19/3481* (2013.01); *G16H 40/63* (2018.01); *A61N 1/36146* (2013.01)

(58) Field of Classification Search
CPC ........... A61N 1/36185; A61N 1/36146; G16H 40/63; G06F 19/3481
USPC .......................................................... 607/60
See application file for complete search history.

(56) References Cited

U.S. PATENT DOCUMENTS

| | | | |
|---|---|---|---|
| 7,822,483 B2 | 10/2010 | Stone et al. | |
| 8,190,250 B2 | 5/2012 | Moffitt | |
| 8,285,389 B2 | 10/2012 | Libbus et al. | |
| 8,452,415 B2 | 5/2013 | Goetz et al. | |
| 8,706,250 B2 | 4/2014 | Zhu et al. | |
| 8,855,773 B2 | 10/2014 | Kokones et al. | |
| 8,874,211 B2 | 10/2014 | Libbus et al. | |
| 8,934,979 B2 | 1/2015 | Moffitt | |
| 9,265,948 B2 | 2/2016 | Libbus et al. | |
| 2009/0281595 A1* | 11/2009 | King | A61N 1/0553 607/46 |
| 2011/0264165 A1 | 10/2011 | Molnar et al. | |
| 2013/0131760 A1 | 5/2013 | Rao et al. | |
| 2014/0122379 A1 | 5/2014 | Moffitt et al. | |
| 2015/0157858 A1 | 6/2015 | McIntyre et al. | |
| 2015/0246233 A1* | 9/2015 | Kaemmerer | A61N 1/36139 607/59 |

OTHER PUBLICATIONS

Carcieri, Stephen, et al., "Methods and Systems for Programming Neuromodulation Devices", U.S. Appl. No. 62/273,508, filed Dec. 31, 2015.
"International Application Serial No. PCT/US2017/017809, International Search Report dated May 10, 2017", 5 pgs.
"International Application Serial No. PCT/US2017/017809, Written Opinion dated May 10, 2017", 5 pgs.

* cited by examiner

METHOD AND APPARATUS FOR INTERLOCKING STIMULATION PARAMETERS FOR NEUROMODULATION

CLAIM OF PRIORITY

This application claims the benefit of priority under 35 U.S.C. § 119(e) of U.S. Provisional Patent Application Ser. No. 62/310,306, filed on Mar. 18, 2016, which is herein incorporated by reference in its entirety.

TECHNICAL FIELD

This document relates generally to neurostimulation and more particularly to a system that interlocks stimulation parameters for programming stimulation devices for neuromodulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device is used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (signals directing the nervous system to respond as desired) aspects of a pattern of neurostimulation pulses. The human nervous systems use neural signals having sophisticated shapes and patterns to communicate various types of information, including sensations of pain, pressure, temperature, etc. It may interpret an artificial stimulation with a simple pattern of stimuli as an unnatural phenomenon, and respond with an unintended and undesirable sensation, response, and/or movement. Also, as the condition of the patient may change while receiving a neurostimulation therapy, the characteristic of the neurostimulation energy applied to the patient may need to be changed to maintain efficacy of the therapy while minimizing the unintended and/or undesirable sensation, response, and/or movement. While modern electronics can accommodate the need for generating sophisticated signals that emulate natural patterns of neural signals observed in the human body, the capability of a neurostimulation system depends on its post-manufacturing programmability to a great extent. For example, a sophisticated pulse pattern may only benefit a patient when it is customized for that patient, with potential interactions between neurostimulation pulses controlled to ensure therapy efficacy and safety. This makes programming of a stimulation device for a patient a challenging task.

SUMMARY

An example (e.g., "Example 1") of a system for delivering neurostimulation to a patient and controlling the delivery of the neurostimulation by a user is provided. The system may include a display and an interface control circuit. The interface control circuit may be configured to define a stimulation waveform according to which the neurostimulation is to be delivered. The stimulation waveform is defined by a plurality of waveform parameters including one or more user-adjustable parameters. The interface control circuit may include a parameter selector, an effect analyzer, and a parameter generator. The parameter selector may be configured to present a plurality of values for each parameter of the one or more user-adjustable parameters on the display and allow the user to select a value for each parameter from the presented plurality of values. The effect analyzer may be configured to estimate an interactive effect of different stimuli of the neurostimulation. The parameter generator may be configured to select a rate rule from a plurality of rate rules based on the estimated interactive effect and to generate the plurality of values for each parameter of the one or more user-adjustable parameters according to the selected rate rule.

In Example 2, the subject matter of Example 1 may optionally be configured such that the effect analyzer is configured to determine volumes of tissue activated (VTAs) each associated with a stimulus of the different stimuli of the neurostimulation, and the parameter generator is configured to select the rate rule from the plurality of rate rules based on the VTAs.

In Example 3, the subject matter of any one or a combination of Examples 1 and 2 may optionally be configured to further include a programming control circuit and a user interface. The programming control circuit is configured to generate a plurality of stimulation parameters controlling delivery of the neurostimulation according to the stimulation waveform. The user interface includes the display and the interface control circuit.

In Example 4, the subject matter of any one or a combination of Examples 1 and 2 may optionally be configured such that the parameter selector is configured to present the plurality of values for each parameter of the one or more user-adjustable parameters on the display as one or more value ranges and allow the user to select a value for each parameter from the one or more value ranges.

In Example 5, the subject matter of any one or any combination of Examples 1 to 4 may optionally be configured such that the effect analyzer is configured to determine the VTAs using one or more biological models.

In Example 6, the subject matter of any one or any combination of Examples 1 to 5 may optionally be configured such that the effect analyzer is configured to determine the VTAs using stimulation field models (SFMs).

In Example 7, the subject matter of any one or a combination of Examples 5 and 6 may optionally be configured such that the effect analyzer is configured to determine the VTAs using patient-specific information related to one or more of size, shape, location, extent, or distribution of each of the VTAs.

In Example 8, the subject matter of any one or any combination of Examples 1 to 7 may optionally be configured such that the parameter generator is configured to generate the plurality of values for each parameter of the one or more user-adjustable parameters such that the VTAs do not spatially overlap.

In Example 9, the subject matter of any one or any combination of Examples 1 to 7 may optionally be configured such that the parameter generator is configured to generate the plurality of values for each parameter of the one or more user-adjustable parameters such that the VTAs have an overlapping volume that is within a specified range.

In Example 10, the subject matter of any one or any combination of Examples 1 to 7 may optionally be configured such that the parameter generator is configured to generate the plurality of values for each parameter of the one or more user-adjustable parameters for controlling an extent to which a common anatomical target indicated by the VTAs is modulated by the different stimuli of the neurostimulation.

In Example 11, the subject matter of any one or any combination of Examples 1 to 7 may optionally be configured such that the parameter generator is configured to generate the plurality of values for each parameter of the one or more user-adjustable parameters for controlling an extent to which a common neural element indicated by the VTAs is modulated by the different stimuli of the neurostimulation.

In Example 12, the subject matter of any one or any combination of Examples 1 to 7 may optionally be configured such that the parameter generator is configured to generate the plurality of values for each parameter of the one or more user-adjustable parameters for controlling an extent to which a common downstream tissue target indicated by the VTAs is modulated by the different stimuli of the neurostimulation.

In Example 13, the subject matter of any one or any combination of Examples 1 to 7 may optionally be configured such that the parameter generator is configured to generate the plurality of values for each parameter of the one or more user-adjustable parameters for controlling an extent to which a common physiological target indicated by the VTAs is modulated by the different stimuli of the neurostimulation.

In Example 14, the subject matter of any one or any combination of Examples 1 to 13 may optionally be configured such that the parameter selector includes a frequency selector configured to allow to user to select a stimulation frequency from a plurality of stimulation frequencies.

In Example 15, the subject matter of any one or any combination of Examples 1 to 7 may optionally be configured such that the frequency selector is configured to present on the display a plurality of stimulation frequencies associated with each area of the plurality of areas of stimulation, and to receive a selection of a stimulation frequency from the presented plurality of stimulation frequencies for that area of the plurality of areas of stimulation.

An example (e.g., "Example 16") of a method for delivering neurostimulation to a patient is also provided. The method includes delivering the neurostimulation according to a stimulation waveform defined by a plurality of waveform parameters including one or more user-adjustable parameters, estimating an interactive effect of different stimuli of the neurostimulation, selecting a rate rule from a plurality of rate rules based on the estimated interactive effect, generating a plurality of values for each parameter of the one or more user-adjustable parameters according to the selected rate rule, presenting the plurality of values for each parameter of the one or more user-adjustable parameters on a display, and allowing a user to select a value for each parameter of the one or more user-adjustable parameters from the plurality of values presented on the display.

In Example 17, the subject matter of estimating the interactive effect as found in Example 16 may optionally include determining volumes of tissue activated (VTAs) each associated with a stimulus of the different stimuli of the neurostimulation, and selecting the rate rule comprises selecting the rate rule from the plurality of rate rules based on the VTAs.

In Example 18, the subject matter of generating the plurality of values for each parameter of the one or more user-adjustable parameters according to the selected rate rule as found in Example 17 may optionally include determining the plurality of values to control an extent to which the VTAs spatially overlap.

In Example 19, the subject matter of generating the plurality of values for each parameter of the one or more user-adjustable parameters according to the selected rate rule as found in any one or a combination of Examples 17 and 18 may optionally include determining the plurality of values to control an extent to which a common target indicated by the VTAs is modulated by the different stimuli of the neurostimulation.

In Example 20, the subject matter of presenting the plurality of values for each parameter as found in any one or any combination of claims 16 to 19 may optionally include presenting a plurality of stimulation frequencies and allowing the user to select the value for each parameter comprises allowing the user to select a stimulation frequency from the presented plurality of stimulation frequencies.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a neurostimulation system with programming rules, user interface, and other features that facilitate programming of stimulation devices for delivering neuromodulation to each patient. In various embodiments, the neurostimulation system can include an implantable device configured to deliver neurostimulation (also referred to as neuromodulation) therapies (such as deep brain stimulation (DBS), spinal cord stimulation (SCS), peripheral nerve stimulation (PNS), vagus nerve stimulation (VNS), etc.) and one or more external devices configured to program the implantable device for its operations and monitor the performance of the implantable device. While DBS is discussed as a specific example, the present subject matter can also be applied to facilitate programming of stimulation devices for delivering various types of neurostimulation therapies. In general, various aspects of the present subject matter as discussed in this document may be applied to any medical system that delivers electrical stimulation to a patient in various embodiments. It is also to be understood that various features of the neurostimulation are discussed in this documents as examples of techniques developed to simplify and/or improve selected aspects of programming of the stimulation devices, rather than all the features needed for the programming.

Figure 1:
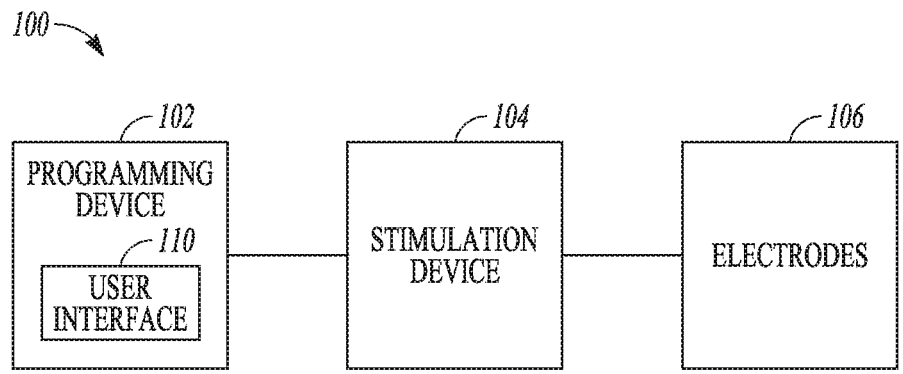
FIG. 1 illustrates an embodiment of a neurostimulation system.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device via a wired or wireless link.

In this document, a "user" includes a physician or other clinician or caregiver who treats the patient using system 100; a "patient" includes a person who receives or is intended to receive neurostimulation delivered using system 100. In various embodiments, the patient is allowed to adjust his or her treatment using system 100 to certain extent, such as by adjusting certain therapy parameters and entering feedback and clinical effects information. While neurostimulation energy delivered in the form of electrical pulses is discussed in various portions of this document as a specific example of stimuli of the neurostimulation, various embodiments may use any type of neurostimulation energy delivered in any type of stimuli that are capable of modulating characteristics and/or activities in neural or other target tissue in a patient.

In various embodiments, programming device 102 includes a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 includes a graphical user interface (GUI) that allows the user to set and/or adjust the values of the user-programmable parameters by creating and/or editing representations of various waveforms, including direct and abstract graphical representations. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 100 can be configured for DBS applications. Such DBS configuration includes various features that may simplify the task of the user in programming stimulation device 104 for delivering DBS to the patient, such as the features discussed in this document.

Figure 2:
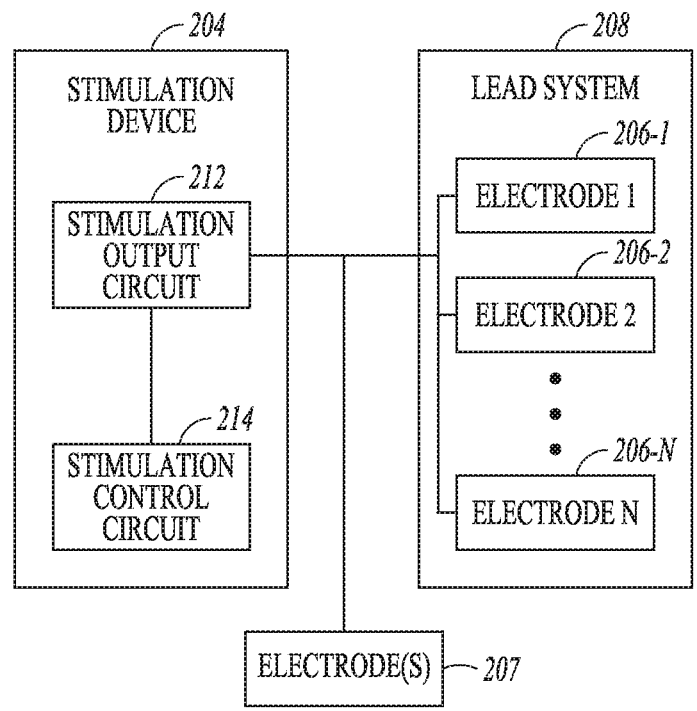
FIG. 2 illustrates an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100. Stimulation device 204 represents an embodiment of stimulation device 104 and includes a stimulation output circuit 212 and a stimulation control circuit 214. Stimulation output circuit 212 produces and delivers neurostimulation pulses. Stimulation control circuit 214 controls the delivery of the neurostimulation pulses from stimulation output circuit 212 using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses or each of collections of pulse intended to be delivered using the same combination of electrodes. In various embodiments, one or more additional electrodes 207 (each of which may be referred to as a reference electrode) can be electrically connected to stimulation device 204, such as one or more electrodes each being a portion of or otherwise incorporated onto a housing of stimulation device 204. Monopolar stimulation uses a monopolar electrode configuration with one or more electrodes selected from electrodes 206 and at least one electrode from electrode(s) 207. Bipolar stimulation uses a bipolar electrode configuration with two electrodes selected from electrodes 206 and none electrode(s) 207. Multipolar stimulation uses a multipolar electrode configuration with multiple (two or more) electrodes selected from electrodes 206 and none of electrode(s) 207.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes.

Figure 3:
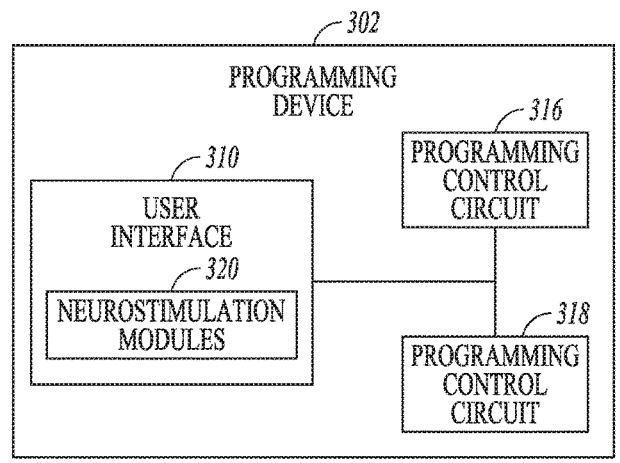
FIG. 3 illustrates an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface 310. Storage device 318 stores one or more stimulation waveforms each represent a pattern of neurostimulation pulses to be delivered during a stimulation period. Programming control circuit 316 generates the plurality of stimulation parameters that controls the delivery of the neurostimulation pulses according to at least one of the stored one or more stimulation waveforms. User interface 310 represents an embodiment of user interface 110 and includes neurostimulation modules 320. In various embodiments, neurostimulation modules 320 are each configured to support one or more functions that facilitate programming of stimulation devices, such as stimulation device 104 including its various embodiments as discussed in this document, for delivering neurostimulation to each patient with safe and efficacious settings. Examples of such one or more functions are discussed below with references to FIG. 9.

In various embodiments, user interface 310 allows for definition of a pattern of neurostimulation pulses for delivery during a neurostimulation therapy session by creating and/or adjusting one or more stimulation waveforms using a graphical method. The definition can also include definition of one or more stimulation fields each associated with one or more pulses in the pattern of neurostimulation pulses. In various embodiments, user interface 310 includes a GUI that allows the user to define the pattern of neurostimulation pulses and perform other functions using graphical methods. In this document, "neurostimulation programming" can include the definition of the one or more stimulation waveforms, including the definition of one or more stimulation fields.

In various embodiments, circuits of neurostimulation 100, including its various embodiments discussed in this document, may be implemented using a combination of hardware and software. For example, the circuit of user interface 110, stimulation control circuit 214, programming control circuit 316, and neurostimulation modules 320, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
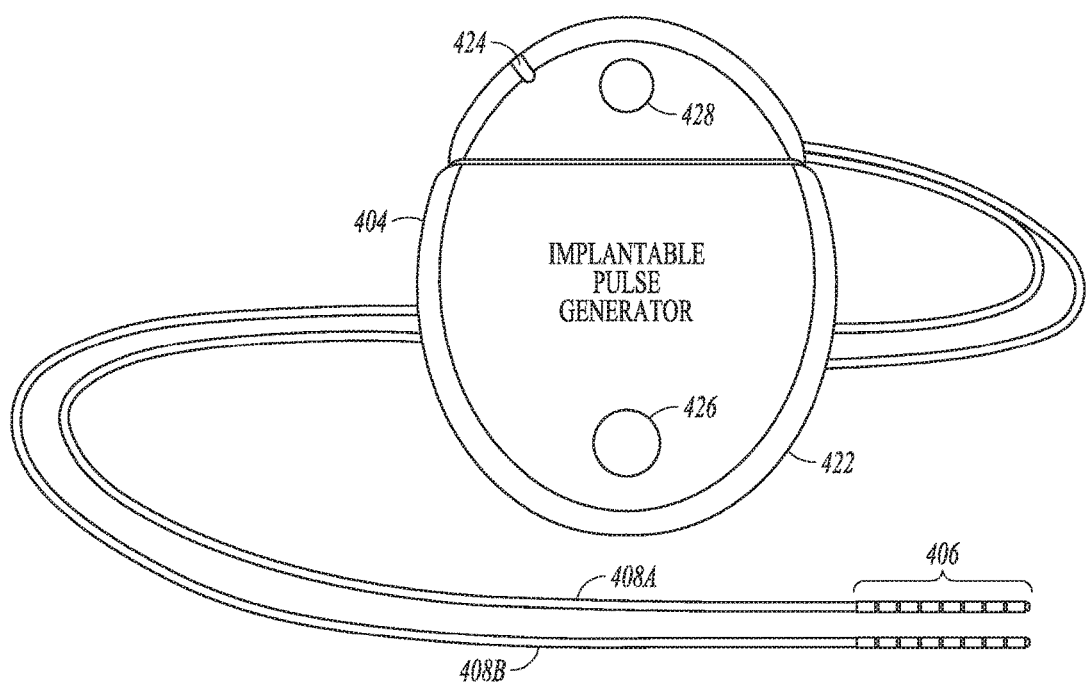
FIG. 4 illustrates an embodiment of an implantable pulse generator (IPG) and an implantable lead system, such as an example implementation of the stimulation device and lead system of FIG. 2.

FIG. 4 illustrates an embodiment of an implantable pulse generator (IPG) 404 and an implantable lead system 408. IPG 404 represents an example implementation of stimulation device 204. Lead system 408 represents an example implementation of lead system 208. As illustrated in FIG. 4, IPG 404 that can be coupled to implantable leads 408A and 408B at a proximal end of each lead. The distal end of each lead includes electrical contacts or electrodes 406 for contacting a tissue site targeted for electrical neurostimulation. As illustrated in FIG. 1, leads 408A and 408B each include 8 electrodes 406 at the distal end. The number and arrangement of leads 408A and 408B and electrodes 406 as shown in FIG. 1 are only an example, and other numbers and arrangements are possible. In various embodiments, the electrodes are ring electrodes. The implantable leads and electrodes may be configured by shape and size to provide electrical neurostimulation energy to a neuronal target included in the subject's brain, or configured to provide electrical neurostimulation energy to a nerve cell target included in the subject's spinal cord.

Figure 5:
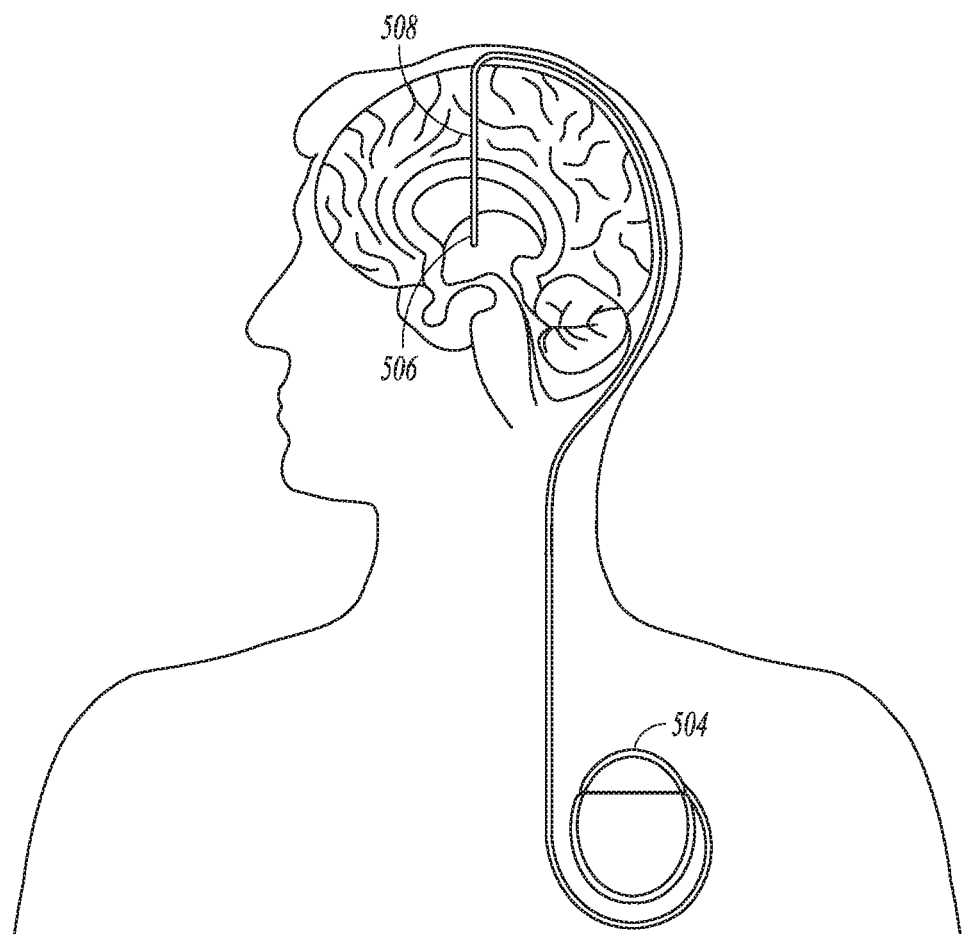
FIG. 5 illustrates an embodiment of an IPG and an implantable lead system, such as the IPG and lead system of FIG. 4, arranged to provide neurostimulation to a patient.

FIG. 5 illustrates an embodiment of an IPG 504 and an implantable lead system 508 arranged to provide neurostimulation to a patient. An example of IPG 504 includes IPG 404. An example of lead system 508 includes one or more of leads 408A and 408B. In the illustrated embodiment, implantable lead system 508 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, and any white matter tracts connecting these and other structures.

Returning to FIG. 4, the IPG 404 can include a hermetically-sealed IPG case 422 to house the electronic circuitry of IPG 404. IPG 404 can include an electrode 426 formed on IPG case 422. IPG 404 can include an IPG header 424 for coupling the proximal ends of leads 408A and 408B. IPG header 424 may optionally also include an electrode 428. Electrodes 426 and/or 428 represent embodiments of electrode(s) 207 and may each be referred to as a reference electrode. Neurostimulation energy can be delivered in a monopolar (also referred to as unipolar) mode using electrode 426 or electrode 428 and one or more electrodes selected from electrodes 406. Neurostimulation energy can be delivered in a bipolar mode using a pair of electrodes of the same lead (lead 408A or lead 408B). Neurostimulation energy can be delivered in an extended bipolar mode using one or more electrodes of a lead (e.g., one or more electrodes of lead 408A) and one or more electrodes of a different lead (e.g., one or more electrodes of lead 408B).

The electronic circuitry of IPG 404 can include a control circuit that controls delivery of the neurostimulation energy. The control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 6:
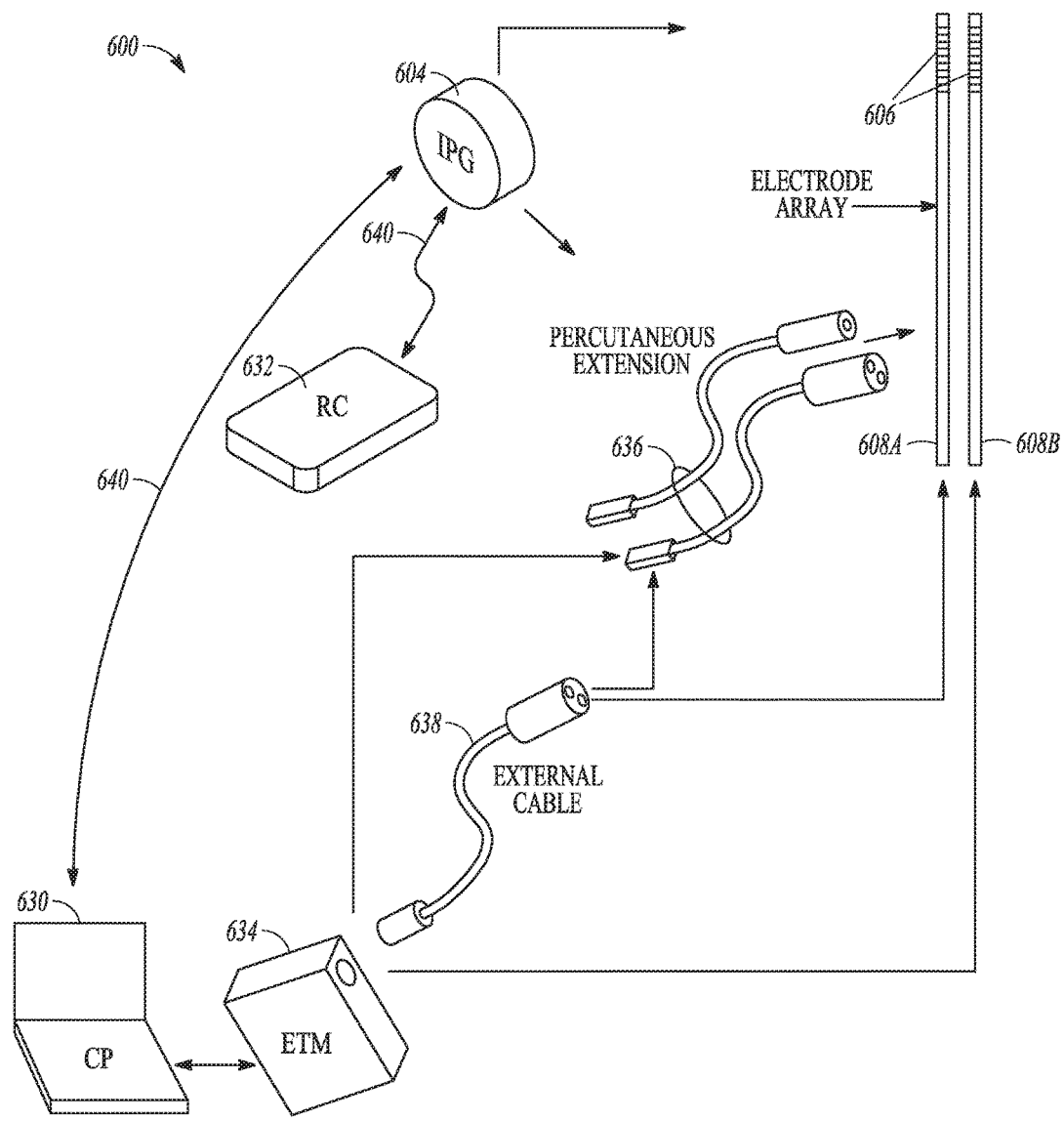
FIG. 6 illustrates an embodiment of portions of a neurostimulation system.

FIG. 6 illustrates an embodiment of portions of a neurostimulation system 600. System 600 includes an IPG 604, implantable neurostimulation leads 608A and 608B, an external remote controller (RC) 632, a clinician's programmer (CP) 630, and an external trial modulator (ETM) 634. IPG 404 may be electrically coupled to leads 608A and 608B directly or through percutaneous extension leads 636. ETM 634 may be electrically connectable to leads 608A and 608B via one or both of percutaneous extension leads 636 and/or external cable 638. System 600 represents an embodiment of system 100, with IPG 604 representing an embodiment of stimulation device 104, electrodes 606 of leads 608A and 608B representing electrodes 106, and CP 630, RC 632, and ETM 634 collectively representing programming device 102.

ETM 634 may be standalone or incorporated into CP 630. ETM 634 may have similar pulse generation circuitry as IPG 604 to deliver neurostimulation energy according to specified modulation parameters as discussed above. ETM 634 is an external device that is typically used as a preliminary stimulator after leads 408A and 408B have been implanted and used prior to stimulation with IPG 604 to test the patient's responsiveness to the stimulation that is to be provided by IPG 604. Because ETM 634 is external it may be more easily configurable than IPG 604.

CP 630 can configure the neurostimulation provided by ETM 634. If ETM 634 is not integrated into CP 630, CP 630 may communicate with ETM 634 using a wired connection (e.g., over a USB link) or by wireless telemetry using a wireless communications link 640. CP 630 also communicates with LPG 604 using a wireless communications link 640.

An example of wireless telemetry is based on inductive coupling between two closely-placed coils using the mutual inductance between these coils. This type of telemetry is referred to as inductive telemetry or near-field telemetry because the coils must typically be closely situated for obtaining inductively coupled communication. IPG 604 can include the first coil and a communication circuit. CP 630 can include or otherwise electrically connected to the second coil such as in the form of a wand that can be place near IPG 604. Another example of wireless telemetry includes a far-field telemetry link, also referred to as a radio frequency (RF) telemetry link. A far-field, also referred to as the Fraunhofer zone, refers to the zone in which a component of an electromagnetic field produced by the transmitting electromagnetic radiation source decays substantially proportionally to 1/r, where r is the distance between an observation point and the radiation source. Accordingly, far-field refers to the zone outside the boundary of $r=\lambda/2\pi$, where $\lambda$ is the wavelength of the transmitted electromagnetic energy. In one example, a communication range of an RF telemetry link is at least six feet but can be as long as allowed by the particular communication technology. RF antennas can be included, for example, in the header of IPG 604 and in the housing of CP 630, eliminating the need for a wand or other means of inductive coupling. An example is such an RF telemetry link is a Bluetooth® wireless link.

CP 630 can be used to set modulation parameters for the neurostimulation after IPG 604 has been implanted. This allows the neurostimulation to be tuned if the requirements for the neurostimulation change after implantation. CP 630 can also upload information from IPG 604.

RC 632 also communicates with IPG 604 using a wireless link 340. RC 632 may be a communication device used by the user or given to the patient. RC 632 may have reduced programming capability compared to CP 630. This allows the user or patient to alter the neurostimulation therapy but does not allow the patient full control over the therapy. For example, the patient may be able to increase the amplitude of neurostimulation pulses or change the time that a pre-programmed stimulation pulse train is applied. RC 632 may be programmed by CP 630. CP 630 may communicate with the RC 632 using a wired or wireless communications link. In some embodiments, CP 630 is able to program RC 632 when remotely located from RC 632.

Figure 7:
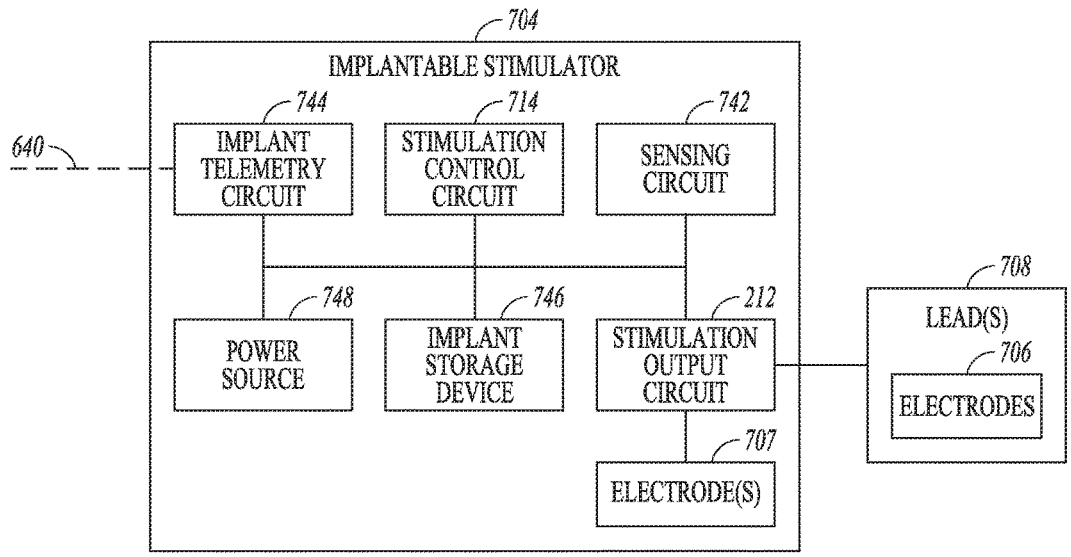
FIG. 7 illustrates an embodiment of an implantable stimulator and one or more leads of an implantable neurostimulation system, such as the implantable neurostimulation system of FIG. 6.

FIG. 7 illustrates an embodiment of implantable stimulator 704 and one or more leads 708 of an implantable neurostimulation system, such as implantable system 600. Implantable stimulator 704 represents an embodiment of stimulation device 104 or 204 and may be implemented, for example, as IPG 604. Lead(s) 708 represents an embodiment of lead system 208 and may be implemented, for example, as implantable leads 608A and 608B. Lead(s) 708 includes electrodes 706, which represents an embodiment of electrodes 106 or 206 and may be implemented as electrodes 606.

Implantable stimulator 704 may include a sensing circuit 742 that is optional and required only when the stimulator needs a sensing capability, stimulation output circuit 212, a stimulation control circuit 714, an implant storage device 746, an implant telemetry circuit 744, a power source 748, and one or more electrodes 707. Sensing circuit 742, when included and needed, senses one or more physiological signals for purposes of patient monitoring and/or feedback control of the neurostimulation. Examples of the one or more physiological signals include neural and other signals each indicative of a condition of the patient that is treated by the neurostimulation and/or a response of the patient to the delivery of the neurostimulation. Stimulation output circuit 212 is electrically connected to electrodes 706 through one or more leads 708 as well as electrodes 707, and delivers each of the neurostimulation pulses through a set of electrodes selected from electrodes 706 and electrode(s) 707. Stimulation control circuit 714 represents an embodiment of stimulation control circuit 214 and controls the delivery of the neurostimulation pulses using the plurality of stimulation parameters specifying the pattern of neurostimulation pulses. In one embodiment, stimulation control circuit 714 controls the delivery of the neurostimulation pulses using the one or more sensed physiological signals. Implant telemetry circuit 744 provides implantable stimulator 704 with wireless communication with another device such as CP 630 and RC 632, including receiving values of the plurality of stimulation parameters from the other device. Implant storage device 746 stores values of the plurality of stimulation parameters. Power source 748 provides implantable stimulator 704 with energy for its operation. In one embodiment, power source 748 includes a battery. In one embodiment, power source 748 includes a rechargeable battery and a battery charging circuit for charging the rechargeable battery. Implant telemetry circuit 744 may also function as a power receiver that receives power transmitted from an external device through an inductive couple. Electrode(s) 707 allow for delivery of the neurostimulation pulses in the monopolar mode. Examples of electrode(s) 707 include electrode 426 and electrode 418 in IPG 404 as illustrated in FIG. 4.

In one embodiment, implantable stimulator 704 is used as a master database. A patient implanted with implantable stimulator 704 (such as may be implemented as IPG 604) may therefore carry patient information needed for his or her medical care when such information is otherwise unavailable. Implant storage device 746 is configured to store such patient information. For example, the patient may be given a new RC 632 and/or travel to a new clinic where a new CP 630 is used to communicate with the device implanted in him or her. The new RC 632 and/or CP 630 can communicate with implantable stimulator 704 to retrieve the patient information stored in implant storage device 746 through implant telemetry circuit 744 and wireless communication link 640, and allow for any necessary adjustment of the operation of implantable stimulator 704 based on the retrieved patient information. In various embodiments, the patient information to be stored in implant storage device 746 may include, for example, positions of lead(s) 708 and electrodes 706 relative to the patient's anatomy (transformation for fusing computerized tomogram (CT) of postoperative lead placement to magnetic resonance imaging (MRI) of the brain), clinical effects map data, objective measurements using quantitative assessments of symptoms (for example using micro-electrode recording, accelerometers, and/or other sensors), and/or any other information considered important or useful for providing adequate care for the patient. In various embodiments, the patient information to be stored in implant storage device 746 may include data transmitted to implantable stimulator 704 for storage as part of the patient information and data acquired by implantable stimulator 704, such as by using sensing circuit 742.

In various embodiments, sensing circuit 742 (if included), stimulation output circuit 212, stimulation control circuit 714, implant telemetry circuit 744, implant storage device 746, and power source 748 are encapsulated in a hermetically sealed implantable housing or case, and electrode(s) 707 are formed or otherwise incorporated onto the case. In various embodiments, lead(s) 708 are implanted such that electrodes 706 are placed on and/or around one or more targets to which the neurostimulation pulses are to be delivered, while implantable stimulator 704 is subcutaneously implanted and connected to lead(s) 708 at the time of implantation.

Figure 8:
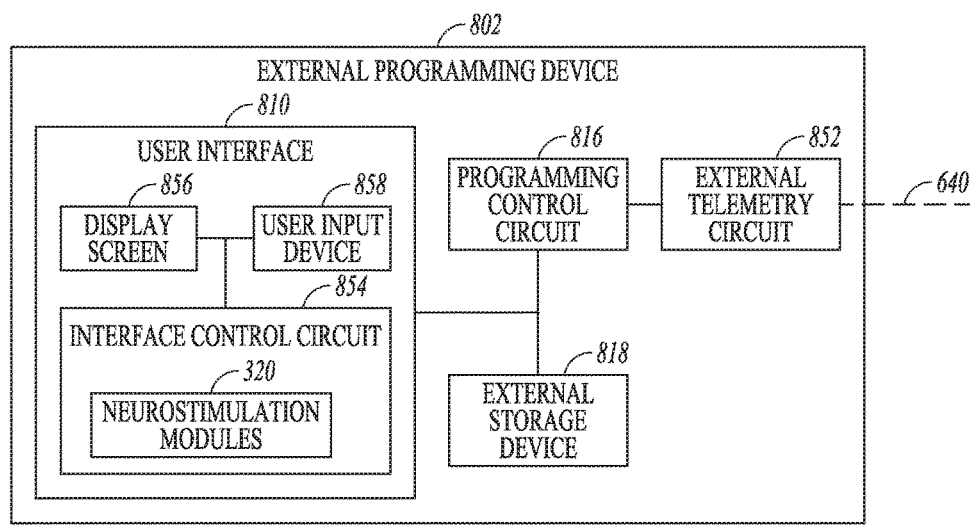
FIG. 8 illustrates an embodiment of an external programming device of an implantable neurostimulation system, such as the implantable neurostimulation system of FIG. 6.

FIG. 8 illustrates an embodiment of an external programming device 802 of an implantable neurostimulation system, such as system 600. External programming device 802 represents an embodiment of programming device 102 or 302, and may be implemented, for example, as CP 630 and/or RC 632. External programming device 802 includes an external telemetry circuit 852, an external storage device 818, a programming control circuit 816, and a user interface 810.

External telemetry circuit 852 provides external programming device 802 with wireless communication with another device such as implantable stimulator 704 via wireless communication link 640, including transmitting the plurality of stimulation parameters to implantable stimulator 704 and receiving information including the patient data from implantable stimulator 704. In one embodiment, external telemetry circuit 852 also transmits power to implantable stimulator 704 through an inductive couple.

In various embodiments, wireless communication link 640 can include an inductive telemetry link (near-field telemetry link) and/or a far-field telemetry link (RF telemetry link). For example, because DBS is often indicated for movement disorders which are assessed through patient activities, gait, balance, etc., allowing patient mobility during programming and assessment is useful. Therefore, when system 600 is intended for applications including DBS, wireless communication link 640 includes at least a far-field telemetry link that allows for communications between external programming device 802 and implantable stimulator 704 over a relative long distance, such as up to about 20 meters. External telemetry circuit 852 and implant telemetry circuit 744 each include an antenna and RF circuitry configured to support such wireless telemetry.

External storage device 818 stores one or more stimulation waveforms for delivery during a neurostimulation therapy session, such as a DBS therapy session, as well as various parameters and building blocks for defining one or more waveforms. The one or more stimulation waveforms may each be associated with one or more stimulation fields and represent a pattern of neurostimulation pulses to be delivered to the one or more stimulation field during the neurostimulation therapy session. In various embodiments, each of the one or more stimulation waveforms can be selected for modification by the user and/or for use in programming a stimulation device such as implantable stimulator 704 to deliver a therapy. In various embodiments, each waveform in the one or more stimulation waveforms is definable on a pulse-by-pulse basis, and external storage device 818 may include a pulse library that stores one or more individually definable pulse waveforms each defining a pulse type of one or more pulse types. External storage device 818 also stores one or more individually definable stimulation fields. Each waveform in the one or more stimulation waveforms is associated with at least one field of the one or more individually definable stimulation fields. Each field of the one or more individually definable stimulation fields is defined by a set of electrodes through a neurostimulation pulse is delivered. In various embodiments, each field of the one or more individually definable fields is defined by the set of electrodes through which the neurostimulation pulse is delivered and a current distribution of the neurostimulation pulse over the set of electrodes. In one embodiment, the current distribution is defined by assigning a fraction of an overall pulse amplitude to each electrode of the set of electrodes. In another embodiment, the current distribution is defined by assigning an amplitude value to each electrode of the set of electrodes. For example, the set of electrodes may include 2 electrodes used as the anode and an electrode as the cathode for delivering a neurostimulation pulse having a pulse amplitude of 4 mA. The current distribution over the 2 electrodes used as the anode needs to be defined. In one embodiment, a percentage of the pulse amplitude is assigned to each of the 2 electrodes, such as 75% assigned to electrode 1 and 25% to electrode 2. In another embodiment, an amplitude value is assigned to each of the 2 electrodes, such as 3 mA assigned to electrode 1 and 1 mA to electrode 2. Control of the current in terms of percentages allows precise and consistent distribution of the current between electrodes even as the pulse amplitude is adjusted. It is suited for thinking about the problem as steering a stimulation locus, and stimulation changes on multiple contacts simultaneously to move the locus while holding the stimulation amount constant. Control and displaying the total current through each electrode in terms of absolute values (e.g. mA) allows precise dosing of current through each specific electrode. It is suited for changing the current one contact at a time (and allows the user to do so) to shape the stimulation like a piece of clay (pushing/pulling one spot at a time).

Programming control circuit 816 represents an embodiment of programming control circuit 316 and generates the plurality of stimulation parameters, which is to be transmitted to implantable stimulator 704, based on the pattern of neurostimulation pulses as represented by one or more stimulation waveforms. The pattern may be created and/or adjusted by the user using user interface 810 and stored in external storage device 818. In various embodiments, programming control circuit 816 can check values of the plurality of stimulation parameters against safety rules to limit these values within constraints of the safety rules. In one embodiment, the safety rules are heuristic rules.

User interface 810 represents an embodiment of user interface 310 and allows the user to define the pattern of neurostimulation pulses and perform various other monitoring and programming tasks. User interface 810 includes a display screen 856, a user input device 858, and an interface control circuit 854. Display screen 856 may include any type of interactive or non-interactive screens, and user input device 858 may include any type of user input devices that supports the various functions discussed in this document, such as touchscreen, keyboard, keypad, touchpad, trackball, joystick, and mouse. In one embodiment, user interface 810 includes a GUI with an interactive screen that displays a graphical representation of a stimulation waveform and allows the user to adjust the waveform by graphically editing the waveform and/or various building blocks of the waveform. The GUI may also allow the user to perform any other functions discussed in this document where graphical editing is suitable as may be appreciated by those skilled in the art.

Interface control circuit 854 controls the operation of user interface 810 including responding to various inputs received by user input device 858 and defining the one or more stimulation waveforms. Interface control circuit 854 includes neurostimulation modules 320.

In various embodiments, external programming device 802 has operation modes including a composition mode and a real-time programming mode. Under the composition mode (also known as the pulse pattern composition mode), user interface 810 is activated, while programming control circuit 816 is inactivated. Programming control circuit 816 does not dynamically updates values of the plurality of stimulation parameters in response to any change in the one or more stimulation waveforms. Under the real-time programming mode, both user interface 810 and programming control circuit 816 are activated. Programming control circuit 816 dynamically updates values of the plurality of stimulation parameters in response to changes in the set of one or more stimulation waveforms, and transmits the plurality of stimulation parameters with the updated values to implantable stimulator 704.

Figures 9, 10:
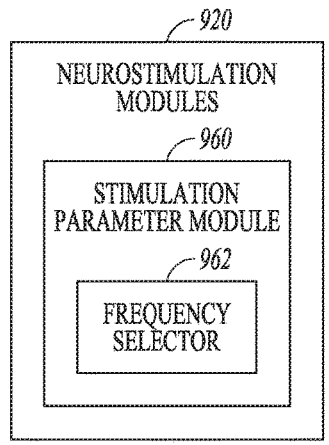
FIG. 9 illustrates an embodiment of portions of a circuit of a user interface of a programming device, such as the external programming device of FIG. 8.
FIG. 10 illustrates an embodiment of portions of a screen displaying stimulation frequencies for selection.

FIG. 9 illustrates an embodiment of neurostimulation modules 920, which represent an embodiment of neurostimulation modules 320. In the illustrated embodiment, neurostimulation modules 920 includes a stimulation parameter module 960. In various embodiments, neurostimulation modules 920 may include one or more other functional modules configured to be used in programming a stimulation device for neurostimulation. Examples of such functional modules are discussed in U.S. Provisional Patent Application No. 62/150,935, entitled "METHOD AND APPARATUS FOR PROGRAMMING DEEP BRAIN STIMULATION DEVICES", filed on Apr. 22, 2015 and U.S. Provisional Patent Application No. 62/273,508, entitled "METHODS AND SYSTEMS FOR PROGRAMMING NEUROMODULATION DEVICES", filed on Dec. 31, 2015, both assigned to Boston Scientific Neuromodulation Corporation, which are incorporated herein by reference in their entirety. In various embodiments, such functional modules may be used individually or in any combination to facilitate the process of defining the one or more stimulation waveforms, and hence the plurality of stimulation parameters, that represent the pattern of neurostimulation pulses to be delivered to the patient during a neurostimulation therapy session.

In the illustrated embodiment, stimulation parameter module 960 includes a frequency selector 962 that allows the user to control stimulation frequency (also referred to as rate) at which the neurostimulation pulses are delivered. In various embodiments, frequency selector 962 allows the user to select between a single frequency mode and a multiple frequency mode. Under the single frequency mode, an adjustment of stimulation frequency in one area of stimulation (e.g., one stimulation field) causes an equivalent change in the stimulation frequency in all the areas of stimulation (e.g., all the stimulation fields) in a neurostimulation session, such that only one stimulation frequency is used at a time. Under the multiple frequency mode, an adjustment of stimulation frequency in one area of stimulation (e.g., one stimulation field) affects the stimulation frequency associated with that area only and does not cause change in the stimulation frequency for another area (e.g., another stimulation field) in a neurostimulation therapy session. In various embodiments that use multiple areas of stimulations in a neurostimulation therapy session, frequency selector 962 computes compatible rates for each area of stimulation and displays them in one or more stimulation rate tables on display screen 856. The compatible (or available) rates for an area of stimulation are stimulation frequencies available for use based on the neurostimulation pulses delivered to all the areas of stimulation. The incompatible (or unavailable) rates may also be displayed, but are not selectable for use. An example of the incompatible rates includes stimulation frequencies at which two or more pulses of the neurostimulation pulses will be delivered to different areas of stimulation simultaneously (i.e., at least partially overlapping in time). Simultaneous delivery of stimulation pulses may decrease therapeutic effectiveness of the neurostimulation.

FIG. 10 illustrates an embodiment of portions of display screen 856 displaying an example of such a stimulation rate table (also referred to as stimulation frequency table) 1072. Stimulation rate table 1072 is discussed as a specific example of present stimulation frequencies for selection. In various embodiments, the stimulation frequencies can be presented on a display in any manner.

Stimulation rate table 1072 presents stimulation frequencies (i.e., rates) for an area of stimulation. In various embodiments, frequency selector 962 limits the stimulation frequencies according to a cumulative rate per lead rule. Under the cumulative rate per lead rule, the user can select any stimulation frequency (i.e., rate) for the areas of stimulation (field) corresponding to a given lead such that the sum of the stimulation frequencies associated with that lead is below a threshold, which may be specified based on safety considerations. An example of the threshold is about 255 Hz. In various embodiments, the threshold may be determined based on data from safety studies. In various other embodiments, the cumulative rate (sum of the stimulation frequencies) may be limited for each electrode or a set of electrodes.

When operating in the multiple frequency mode, it may be desirable to prevent pulses from different timing channels from being delivered simultaneously (such that two or more pulses overlap in time). The timing channels each identify a set of one or more electrodes selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the timing channels. In one embodiment, frequency selector 962 provides for (1) a limitation option, in which the available combinations of stimulation frequencies are limited, or (2) an arbitration option, in which timing of delivery of neurostimulation pulses from a timing channel can be slightly modified (e.g., delayed) when needed, introducing some variability in the inter-pulse interval (IPI) for that timing channel. In one embodiment, stimulation frequency module 966 allows the user to select between the limiting and arbitration options, i.e., (1) and (2). When the arbitration option is selected, frequency selector 962 causes the degree of the variability in IPI for any combination of stimulation frequencies on display screen 856 as a percentage of the stimulation pulses that are delayed, as a standard deviation in the IPI, and/or through other descriptive statistics.

Figure 13:
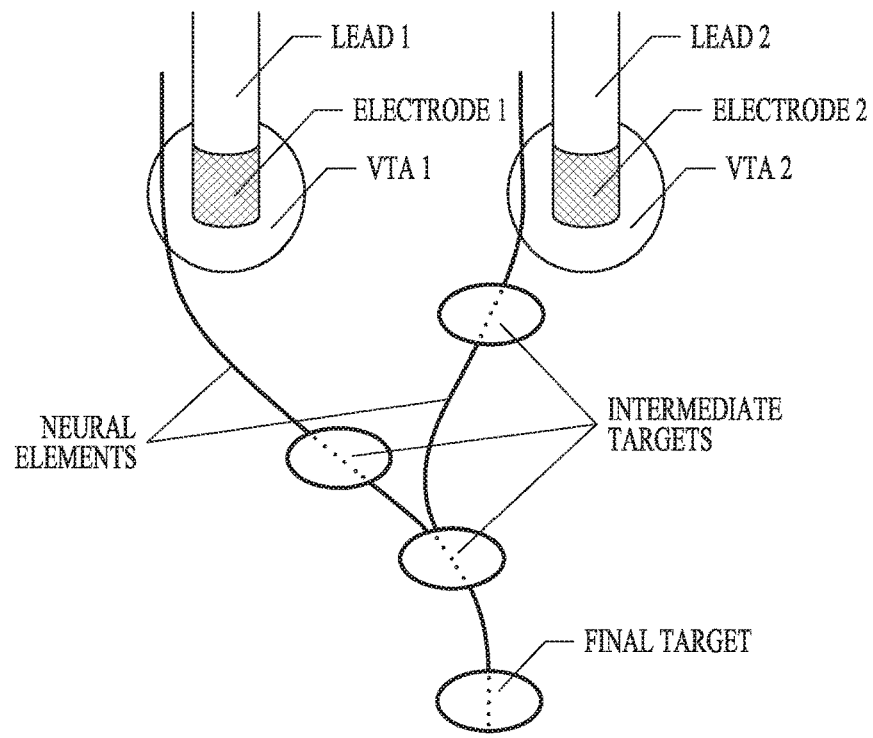
FIG. 13 illustrates an example of a common upstream or downstream target stimulated by neurostimulation pulses delivered from different electrodes.

In the illustrated embodiment, stimulation rate table 1072 includes all the stimulation frequencies, with each of the stimulation frequencies indicated to be (a) selected, (b) available for selection (compatible), or (c) unavailable for selection (incompatible) or available for selection after arbitration. Examples for (a), (b), and (c) are illustrated in FIG. 13 as displaying areas 1074, 1076, and 1078, respectively, in which each stimulation frequency is indicated to be one of (a), (b), or (c) using gray scale. In other embodiments, each stimulation frequency may be indicated to be one of (a), (b), or (c) using color, pattern, or any other visually distinguishable features. If the user selects the limitation option, the stimulation frequencies indicated to be (c), e.g., 1078, are displayed but not selectable by the user. If the user selects the arbitration option, the stimulation frequencies indicated to be (c), e.g., 1078, as displayed are each selectable by the user but associated with a modification of timing (e.g., introduction of delays) in delivering the neurostimulation pulses resulting from the arbitration. In various embodiments, stimulation frequency module 966 causes the plurality of stimulation frequencies to be displayed on screen 856 with each stimulation frequency visually indicated to be (a), (b), or (c). When the arbitration option is selected, stimulation frequency module 966 causes the plurality of stimulation frequencies to be displayed on screen 856 with visual indications for the stimulation frequencies to which the arbitration is performed and/or the degree to which arbitration is performed for that combination of stimulation frequencies.

In one embodiment, stimulation rate table 1072 allows for selection of all stimulation frequencies, including stimulation frequencies for which the arbitration is performed. No stimulation frequency is unavailable in stimulation rate table 1072 (i.e., all the stimulation frequencies are selectable), but the stimulation frequencies for which the arbitration is performed are indicated in stimulation rate table 1072. In one embodiment, the stimulation frequencies for which the arbitration is performed are indicated with showing of the degree of resulting variability in the IPI in stimulation rate table 1072.

In various embodiments, using stimulation rate table 1072 allows the user to skip directly to desired stimulation frequencies without having to pass through unwanted combinations of frequencies. Stimulation rate table 1072 also allows the user to compare a complete list of available combinations of the stimulation frequencies before choosing the best combination.

In various embodiments, the stimulation frequencies displayed in stimulation rate table 1072, as well as various other stimulation parameters, are determined based on analysis of interactions between different stimuli of the neurostimulation. An example of such different stimuli includes neurostimulation delivered from different electrodes. FIGS. 11-14 illustrate some examples of scenarios in which interactions between neurostimulation delivered from different electrodes may have effect on therapeutic outcome. These examples are for illustrative purposes only, are not intended to be an exhaustive or exclusive collection of possible scenarios, and may reflect only a portion of a complete electrode set used in a neuromodulation therapy. In various embodiments, the different stimuli of the neurostimulation may include spatially and/or temporally different stimuli.

In the following discussion, an active electrode refers to an electrode selected from a plurality of electrodes in a neurostimulation system that is selected for delivering neurostimulation pulses in each example. In each of FIGS. 11-14, an active Electrode 1 and an active Electrode 2 are illustrated. A first volume of tissue activated (VTA 1) results from neurostimulation pulses delivered through Electrode 1. A second volume of tissue activated (VTA 2) results from neurostimulation pulses delivered through Electrode 2.

VTA 1 and VTA 2 may result from neurostimulation pulses that are overlapping, partially overlapping, or non-overlapping in time, while the time delays of the VTAs with respect to the target of the neurostmulation result in the target being modulated by the neurostimulation pulses through both VTA 1 and VTA 2. For example, VTA 1 and VTA 2 may be non-overlapping in time, but the time delay associated with each of VTA 1 and VTA 2 with respect to an upstream or downstream target is such that the modulation effect on the target results from both VTA 1 and VTA 2. When the modulation effect is undesirable, such a relationship between VTA1 and VTA2 may be warned to the user and/or prevented. When the modulation effect is desirable, such a relationship between VTA 1 and VTA2 is allowed, and the relatively timing between VTA 1 and VTA 2 may be adjusted or optimized for benefiting from this relationship. The target is modulated when a physiological response is evoked by the delivery of the neurostimulaton pulses. The modulation may include, for example, supra-threshold stimulation that evokes one or more neural action potentials or sub-threshold stimulation that modulates one or more characteristics of the target tissue without evoking an active potential.

Figure 11:
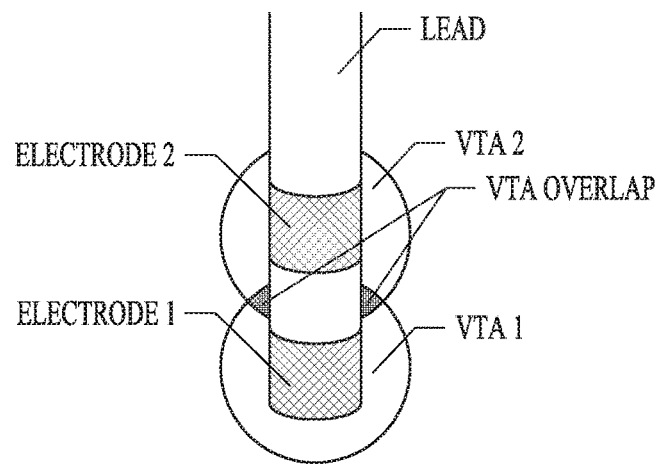
FIG. 11 illustrates an example of partially overlapping volumes of tissue activated by neurostimulation pulses delivered from different electrodes.

FIG. 11 illustrates an example of partially overlapping volumes of tissue activated (VTAs) by neurostimulation pulses delivered from different electrodes. VTA 1 and VTA2 partially overlap in space and have a common volume (VTA Overlap).

Figure 12:
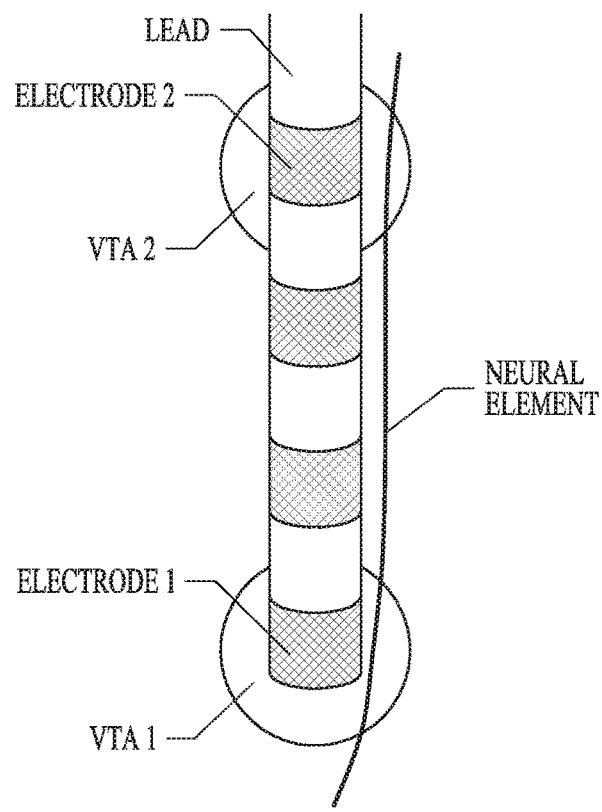
FIG. 12 illustrates an example of a common neural element stimulated by neurostimulation pulses delivered from different electrodes.

FIG. 12 illustrates an example of a common neural element stimulated by neurostimulation pulses delivered from different electrodes. In this document, a "common neural element" refers to an anatomic unit of the nervous system (e.g., a particular nerve or nerve branch) that is stimulated or targeted by neurostimulation energy from different sources (e.g., neurostimulation pulses delivered from different electrodes). VTA 1 and VTA 2 do not spatially overlap, but each include a portion of a common neural element such that the common neural element may be modulated by neurostimulation pulses delivered through both Electrode 1 and Electrode 2.

FIG. 13 illustrates an example of a common upstream or downstream target stimulated by neurostimulation pulses delivered from different electrodes. VTA 1 and VTA 2 do not spatially overlap, but each include a portion of a neural element connected to a common upstream or downstream target such that the upstream or downstream target may be stimulated by neurostimulation pulses delivered through both Electrode 1 and Electrode 2. In the illustrated example, the final target of the neurostimulation, which may be upstream or downstream from VTA 1 and VTA 2, is coupled to VTA 1 and VTA 2 through neural elements and intermediate targets. The intermediate targets may each be modulated by the neurostimulation pulses delivered through Electrode 1 only, Electrode 2 only, or both Electrode 1 and Electrode 2. The common final target may be modulated by the neurostimulation pulses through both Electrode 1 and Electrode 2.

Figure 14:
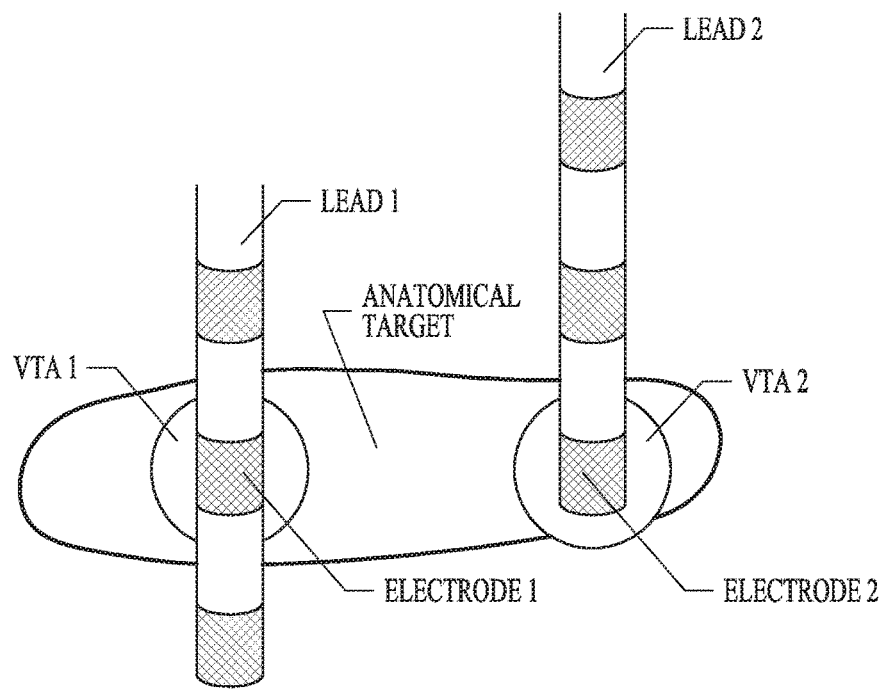
FIG. 14 illustrates an example of a common anatomical target stimulated by neurostimulation pulses delivered from different electrodes.

FIG. 14 illustrates an example of a common anatomical target stimulated by neurostimulation pulses delivered from different electrodes. VTA 1 and VTA 2 do not spatially overlap, but each include a portion of a common anatomical target such that the anatomical target may be modulated by neurostimulation pulses delivered through both Electrode 1 and Electrode 2.

In various embodiments, the VTAs may be estimated based on, for example, visualization of Stimulation Field Models (SFMs). Combinations of stimulation parameters that do not result in overlapping SFMs are not subject to the rate rule because they do not stimulate the same volume of tissue. Combinations of stimulation parameters that do result in overlapping SFMs are limited to certain compatible combinations of rates. Thus, values of stimulation parameters are limited such that interactions between neurostimulation pulses are managed according to a set of desirable outcomes.

In various embodiments, all target tissue to be modulated by neurostimulation is modulated at the same rate (stimulation frequency) by all stimulating fields. In other words, no portion of the target tissue should be stimulated at a different rate (resulting from different stimulation frequencies applied for different stimulation fields). The amount of stimulation from each active electrode may be limited, given the amount of stimulation from other active electrodes, such that the VTAs from each active electrode do not overlap. In various other embodiments, instead of avoiding overlap of the VTAs, some amount of overlap of the VTAs is permitted according to some rules. For example, the rules may ensure that total overlapping VTA amount is less than a given threshold, or total amount of secreted/emitted/dispersed neurotransmitter or compound is less than or greater than a thresholds.

Figure 15:
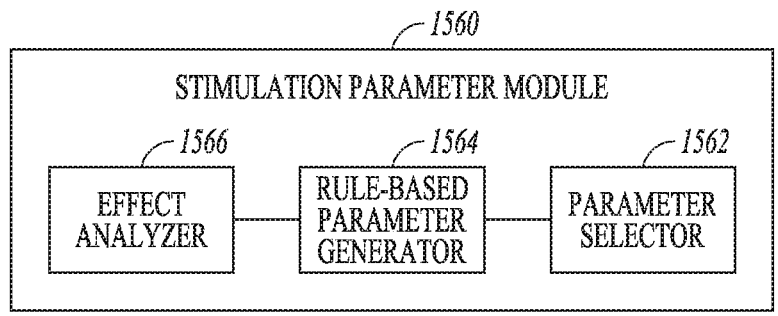
FIG. 15 illustrates an embodiment of a stimulation parameter module of a circuit of a user interface, such as the circuit of FIG. 9.

FIG. 15 illustrates an embodiment of a stimulation parameter module 1560, which represents an embodiment of stimulation parameter module 960. Stimulation parameter module 1560 includes a parameter selector 1562, an effect analyzer, and a rule-based parameter generator 1564. Stimulation parameter module 1560 allows for setting values for a plurality of waveform parameters defining a stimulation waveform according to which the neurostimulation is to be delivered. In one embodiment, stimulation parameter module 1560 allows for setting values for a plurality of waveform parameters defining a stimulation waveform according to which neurostimulation pulses are to be delivered using a set of active electrodes selected from a plurality of electrodes such as the electrode sets or arrays discussed above in this document. The plurality of waveform parameters includes one or more user-adjustable parameters.

Parameter selector 1562 can present a plurality of values for each parameter of the one or more user-adjustable parameters on display screen 856 and allow the user to select a value for each parameter from the plurality of values presented on display screen 856. In one embodiment, parameter selector 1562 includes frequency selector 962. In various embodiments, the plurality of values can be presented as a value table, such as stimulation rate table 1072, and/or presented as one or more value ranges.

Effect analyzer 1566 can determine an interactive effect of different stimuli of the neurostimulation. The interactive effect is a modulation of a tissue site or circuit resulting from more than one stimulus of the neurostimulation. The different stimuli may include stimuli delivered in different spatial and temporal manners. When the neurostimulation is delivered as electrical pulses, the stimuli can include a pulse or a group of pulses, and the different stimuli can include pulses or groups of pulses defined by different spatial parameters (e.g., selection of active electrodes) and/or different temporal parameters (e.g., stream of pulses delivered through different timing channel each associated with a set of one or more active electrodes). Effect analyzer 1566 can determine the interactive effect of, for example, pulses delivered from one or more active electrodes of the set of active electrodes. In various embodiments, the effect is determined using physiological modeling and/or other means allowing for estimation of amount of modulation of a target of the neurostimulation resulting from delivery of neurostimulation pulses from different active electrodes and/or different timing channels. In various embodiments, effect analyzer 1566 can determine volumes of tissue activated (VTAs) each associated a stimulus of the different stimuli of the neurostimulation. In one embodiment, effect analyzer 1566 can determine VTAs each associated with an active electrode of the set of active electrodes through which the neurostimulation pulses are delivered. In one embodiment, effect analyzer 1566 estimates the VTAs using one or more biological models. In one embodiment, effect analyzer 1566 estimates the VTAs using stimulation field models (SFMs). In various embodiments, effect analyzer 1566 computes the VTAs using modeling without any patient-specific information that allows for customization of the plurality of waveform parameters for each individual patient. In various other embodiments, effect analyzer 1566 computes the VTAs using modeling and patient-specific information such as patient demographic information, indication information, magnetic resonance imaging (MRI), computerized tomography (CT), diffusion tensor imaging (DTI), other imaging data, bloodwork data, or other patient-specific data, which may modulate the size, shape, location, extend, distribution, etc., of the VTAs, or of other parameters used to interlock the waveform parameters.

In various embodiments, a VTA, also referred to as volume of activation (VOA), may be estimated for a set of stimulation parameters based on modeling of electrodes and tissue, for predicting effects of neurostimulation. Examples of such modeling and VTA estimation are discussed in U.S. Pat. No. 8,190,250 B2, entitled "SYSTEM AND METHOD FOR ESTIMATING VOLUME OF ACTIVATION IN TISSUE", U.S. Pat. No. 8,706,250 B2, entitled "NEUROSTIMULATION SYSTEM FOR IMPLEMENTING MODEL-BASED ESTIMATE OF NEUROSTIMULATION EFFECTS", U.S. Pat. No. 8,934,979 B2, entitled "NEUROSTIMULATION SYSTEM FOR SELECTIVELY ESTIMATING VOLUME OF ACTIVATION AND PROVIDING THERAPY", U.S. Patent Application Publication No. 2014/0122379 A1, entitled "SYSTEMS AND METHODS FOR VOA MODEL GENERATION AND USE", all assigned to Boston Scientific Neuromodulation Corporation, which are incorporated by reference herein in their entirety.

Parameter generator 1564 can select a rate rule from a plurality of rate rules based on the estimated interactive effect and to generate the plurality of values for each parameter of the one or more user-adjustable parameters according to the selected rate rule. An example for the rate rule includes the cumulative rate per lead rule discussed above. In one embodiment, parameter generator 1564 can select a rate rule from a plurality of rate rules based on the VTAs and generate the plurality of values for each parameter of the one or more user-adjustable parameters according to the selected rate rule. In various embodiments, parameter generator 1564 generates the plurality of values by adjusting existing values or value ranges, such as default values or value ranges.

In this document, a "rate rule" includes a rule that governs or restricts how one or more stimulation rates can be allowed (e.g., programmed) based on one or more interactive effects of different stimuli delivered at the one or more stimulation rates. A "stimulation rate" for neurostimulation can refer to the number of cycles per second. That is, there is a single unit of time and a single bolus of phases of stimulation within that unit (e.g., a first phase, or stimulation phase, defined by an amplitude and pulse width, followed by a second phase, or recharge phase, of opposite polarity to the first phase to recover the charges injected in the first phase. The stimulation rate can therefore be considered as a duty cycle, where a fraction is defined such that the numerator is the duration of time where charge is being moved by the system (injected/withdrawn), and the denominator is the total duration of the cycle (e.g., 1 second). With new types of stimulation, there can be additional hierarchies of duty cycles, such that a first rate (e.g., 130 Hz for DB) may be modulated in an on-and-off fashion by additional, longer-duration cycles (e.g., 1 Hz, i.e., 1 second on, 1 second off, and so on). These durations can be symmetric, (e.g., 1 second on, 1 second off) or asymmetric (e.g., 1 second on, 3 seconds off). A plurality of such modulations can be stacked. A stimulation approach referred to as Coordinated Reset stimulation involves multiple of these hierarchies of duty cycles (stimulation rates). For example, stimulation bursts of 130 Hz can be alternated between fields for durations of 77 ms. A collection of 10 bursts may be called a Cycle, and Cycles played for 2 on (154 ms), 10 off (770 ms) may each be called a micro-schedule, whereby micro-scheduled stimulation may be on for 2 hours (a period called a bolus or dose) followed by off for 10 hours, such that a 24-hour repeating pattern is defined. The stimulation rates at these various hierarchies are implicated in the present subject matter. Certain of the levels of the hierarchy are more or less amenable to analysis using SFMs, but all levels can be integrated into various biological models.

Examples of the rate rules include, but are not limited to, determining the plurality of values for each parameter of the one or more user-adjustable parameters:

for controlling an extent to which the VTAs spatially overlap;
such that the VTAs do not spatially overlap;
such that the VTAs have an overlapping volume that is under a specified volume;
such that the VTAs have an overlapping volume that exceeds a specified volume;

for controlling an extent to which a common anatomical target is modulated by different stimuli of the neurostimulation;
such that the common anatomical target indicated by the VTAs is not modulated by different stimuli of the neurostimulation;
such that the common anatomical target indicated by the VTAs is modulated by different stimuli of the neurostimulation;

for controlling an extent to which a common neural element indicated by the VTAs is modulated by different stimuli of the neurostimulation;
such that the common neural element indicated by the VTAs is not activated by different stimuli of the neurostimulation;
such that the common neural element indicated by the VTAs is modulated by different stimuli of the neurostimulation;
such that the common neural element indicated by the VTAs is modulated to a measurable amount by different stimuli of the neurostimulation;
the measurable amount within a specified range;
the measurable amount below a threshold amount;
the measurable amount above a threshold amount;

for controlling an extent to which a common upstream or downstream tissue target indicated by the VTAs is modulated by different stimuli of the neurostimulation;
such that the common upstream or downstream tissue target indicated by the VTAs is not modulated by different stimuli of the neurostimulation;

such that the common upstream or downstream tissue target indicated by the VTAs is modulated by different stimuli of the neurostimulation;

for controlling an extent to which a common physiological target indicated by the VTAs is not modulated by different stimuli of the neurostimulation;

such that a common physiological target indicated by the VTAs is not modulated by different stimuli of the neurostimulation;

such that a common physiological target indicated by the VTAs is modulated by different stimuli of the neurostimulation.

In various embodiments, the different stimuli of the neurostimulation may include spatially and/or temporally different stimuli. In the example of neurostimulation pulses, spatially different stimuli may include pulses delivered from different electrodes, and temporally different stimuli may include pulses delivered at different times or pulses of different pulse groups defined by different set of temporal parameters. In various embodiments, two or more of such rate rules that are not mutually exclusive may be applied simultaneously. In various embodiments, such rate rules may be implemented as decision trees or state machines for determining the plurality of values for each user-adjustable parameter of the plurality of waveform parameters.

Figure 16:
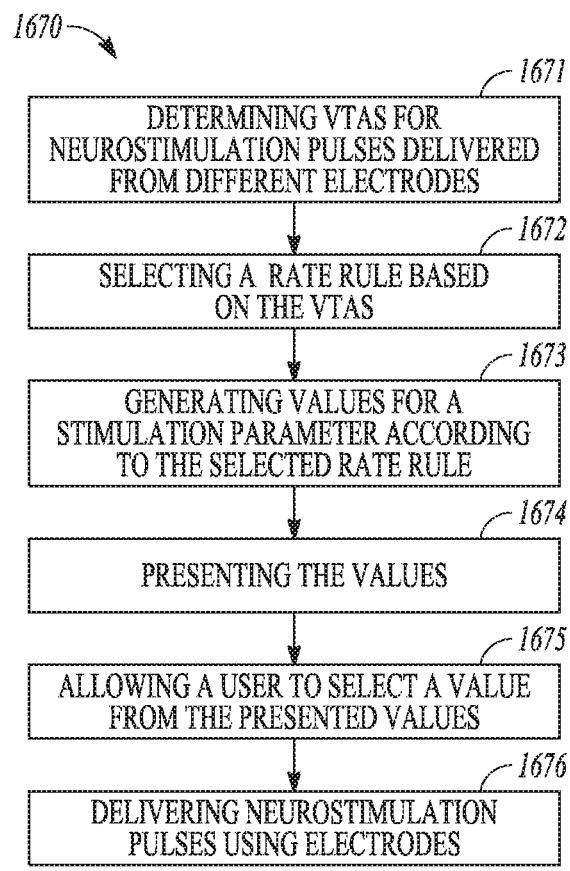
FIG. 16 illustrates a flow chart of a method for determining stimulation parameter values based on estimated effects of neurostimulation pulses delivered through different electrodes.

FIG. 16 illustrates a flow chart of a method 1670 for determining stimulation parameter values based on estimated effects of neurostimulation pulses delivered through different electrodes. In one embodiment, method 1670 is performed by system 100, including its various embodiments as discussed in this document. In various embodiments, the neurostimulation pulses are delivered according to a stimulation waveform to a set of active electrodes selected from a plurality of electrodes of a neurostimulation system. The stimulation waveform is defined by a plurality of waveform parameters including one or more user-adjustable parameters. While neurostimulation pulses are discussed as a specific example of stimuli of neurostimulation, method 1670 may be applied using any form of neurostimulation energy and stimuli in various embodiments.

At 1671, VTAs each associated with an active electrode of the set of active electrodes are determined. In various embodiments, the VTAs are estimated using one or more biological models capable of modeling a patient's physiological response to various stimulation parameters. An example is to estimate the VTAs using SFMs.

At 1672, a rate rule is selected from a plurality of rate rules based on the VTAs. The rate rules each relate values of the one or more user-adjustable parameters to a desirable therapeutic outcome.

The VTAs are discussed as a specific example of means for analyzing the effect of neurostimulation. In various embodiments, the effect of neurostimulation may be determined using physiological modeling and/or other means allowing for estimation of amount of modulation of a target of the neurostimulation resulting from delivery of neurostimulation pulses from different active electrodes. In various embodiments, an effect of energy of the neurostimulation delivered from two or more active electrodes of the set of active electrodes is estimated at 1671, and a rate rule is selected from a plurality of rate rules based on the estimated effect at 1672.

At 1673, a plurality of values is generated for each user-adjustable parameter according to the selected rate rule. Examples of the rate rules are discussed above. In various embodiments, the plurality of values for each user-adjustable parameter is determined to control an extent to which the VTAs overlap. The extent may be specified as no overlap, a permissible overlap up to a certain threshold, or a permissible overlap of at least a certain threshold. In various embodiments, the plurality of values for each user-adjustable parameter is determined to control an extent to which a common target indicated by the VTAs is modulated by different stimuli of the neurostimulation, such as more than one pulse of the neurostimulation pulses. The extent may be measured by one or more sensed or observed parameters and specified by threshold values of these parameters.

At 1674, the plurality of values generated for each user-adjustable parameter is presented on a display screen. In one embodiment, the plurality of values is presented as a table listing all the values. In another embodiment, the plurality of values is presented as one or more values ranges. On example for the one or more user-adjustable parameters is the stimulation frequency (rate), whose values may be presented in a stimulation rate table such as stimulation rate table 1072 as illustrated in FIG. 10 and discussed above with reference to FIG. 10.

At 1675, the user is allowed to select a value for each user-adjustable parameter from the plurality of values presented on the display screen. At 1676, neurostimulation pulses are delivered according to the stimulation waveform defined by the plurality of waveform parameters including the one or more user-adjustable parameters, using the value(s) of the one or more user-adjustable parameters selected by the user at 1675. In various embodiments, the neurostimulation pulses are delivered from an implantable, external, or percutaneous stimulation system that includes a stimulation device programmed with the plurality of waveform parameters. After selecting value(s) for the one or more user-adjustable parameters at 1675, the user may program the stimulation device to start the delivery of the neurostimulation pulses at 1676.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient and controlling the delivery of the neurostimulation by a user, the system comprising:

a display; and an interface control circuit configured to define a stimulation waveform according to which the neurostimulation is to be delivered, the stimulation waveform defined by a plurality of waveform parameters including one or more user-adjustable parameters, the interface control circuit including:

a parameter selector configured to present a plurality of values for each parameter of the one or more user-adjustable parameters on the display and allow the user to select a value for each parameter from the presented plurality of values;

an effect analyzer configured to estimate an interactive effect of different stimuli of the neurostimulation, the interactive effect including modulation of a target of the neurostimulation resulting from interaction among the different stimuli; and a parameter generator configured to select a rate rule from a plurality of rate rules based on the estimated interactive effect and to generate the plurality of values for each parameter of the one or more user-adjustable parameters according to the selected rate rule, the rate rules each restricting availability of one or more stimulation rates for use as a parameter of the plurality of waveform parameters according to a type of the interaction among the different stimuli.

2. The system of claim 1, wherein the effect analyzer is configured to determine volumes of tissue activated (VTAs) each associated with a stimulus of the different stimuli, and the parameter generator is configured to select the rate rule from the plurality of rate rules based on the VTAs.

3. The system of claim 2, further comprising:
a programming control circuit configured to generate a plurality of stimulation parameters controlling delivery of the neurostimulation according to the stimulation waveform; and
a user interface coupled to the programming control circuit and including the display and the interface control circuit.

4. The system of claim 2, wherein the parameter selector is configured to present the plurality of values for each parameter of the one or more user-adjustable parameters on the display as one or more value ranges and allow the user to select a value for each parameter from the one or more value ranges.

5. The system of claim 2, wherein the effect analyzer is configured to determine the VTAs using one or more biological models.

6. The system of claim 2, wherein the effect analyzer is configured to determine the VTAs using stimulation field models (SFMs).

7. The system of claim 2, wherein the effect analyzer is configured to determine the VTAs using patient-specific information related to one or more of size, shape, location, extent, or distribution of each of the VTAs.

8. The system of claim 2, wherein the parameter generator is configured to generate the plurality of values for each parameter of the one or more user-adjustable parameters such that the VTAs do not spatially overlap.

9. The system of claim 2, wherein the parameter generator is configured to generate the plurality of values for each parameter of the one or more user-adjustable parameters such that the VTAs have an overlapping volume that is within a specified range.

10. The system of claim 2, wherein the parameter generator is configured to generate the plurality of values for each parameter of the one or more user-adjustable parameters for controlling an extent to which a common anatomical target indicated by the VTAs is modulated by the different stimuli of the neurostimulation.

11. The system of claim 2, wherein the parameter generator is configured to generate the plurality of values for each parameter of the one or more user-adjustable parameters for controlling an extent to which a common neural element indicated by the VTAs is modulated by the different stimuli of the neurostimulation.

12. The system of claim 2, wherein the parameter generator is configured to generate the plurality of values for each parameter of the one or more user-adjustable parameters for controlling an extent to which a common downstream tissue target indicated by the VTAs is modulated by the different stimuli of the neurostimulation.

13. The system of claim 2, wherein the parameter generator is configured to generate the plurality of values for each parameter of the one or more user-adjustable parameters for controlling an extent to which a common physiological target indicated by the VTAs is modulated by the different stimuli of the neurostimulation.

14. The system of claim 2, wherein the parameter selector comprises a frequency selector configured to allow to user to select of a stimulation frequency from a plurality of stimulation frequencies.

15. The system of claim 14, wherein the frequency selector is configured to present on the display a plurality of stimulation frequencies associated with each area of the plurality of areas of stimulation, and to receive a selection of a stimulation frequency from the presented plurality of stimulation frequencies for that area of the plurality of areas of stimulation.

16. The system of claim 2, wherein the plurality of rate rules comprises a rate rule for controlling an extent to which the VTAs spatially overlap.

17. The system of claim 2, wherein the plurality of rate rules comprises a rate rule for controlling an extent to which a common anatomical target is modulated by the different stimuli.

18. The system of claim 2, wherein the plurality of rate rules comprises a rate rule for controlling an extent to which a common neural element indicated by the VTAs is modulated by the different stimuli.

19. The system of claim 2, wherein the plurality of rate rules comprises a rate rule for controlling an extent to which a common upstream or downstream tissue target indicated by the VTAs is modulated b the different stimuli.

20. The system of claim 2, wherein the plurality of rate rules comprises a rate rule for controlling an extent to which a common physiological target indicated by the VTAs is not modulated b the different stimuli.

* * * * *